US009382569B1

(12) United States Patent
Wiederin

(10) Patent No.: US 9,382,569 B1
(45) Date of Patent: Jul. 5, 2016

(54) FAST DETECTION OF THE PRESENCE OF A TARGET MICROBE IN A LIQUID SAMPLE

(71) Applicant: Elemental Scientific, Inc., Omaha, NE (US)

(72) Inventor: Daniel R. Wiederin, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 0 days.

(21) Appl. No.: 13/742,433

(22) Filed: Jan. 16, 2013

Related U.S. Application Data

(60) Provisional application No. 61/587,252, filed on Jan. 17, 2012.

(51) Int. Cl.
*G01N 21/00* (2006.01)
*C12Q 1/04* (2006.01)

(52) U.S. Cl.
CPC ....................................... *C12Q 1/04* (2013.01)

(58) Field of Classification Search
CPC ...... C12M 41/06; C12M 31/00; G01N 21/74; G01N 21/763; G01N 21/76; B01L 2300/0654
See application file for complete search history.

(56) References Cited

U.S. PATENT DOCUMENTS

| 5,100,626 | A | * | 3/1992 | Levin ............................ 422/424 |
| 5,858,770 | A | * | 1/1999 | Perlman ..................... 435/305.3 |
| 6,190,878 | B1 | * | 2/2001 | Pierson et al. .................. 435/34 |
| 7,410,615 | B2 | * | 8/2008 | Krug et al. ..................... 422/521 |
| 8,280,471 | B2 | * | 10/2012 | Rainone et al. ............... 600/310 |
| 2005/0239197 | A1 | * | 10/2005 | Katerkamp et al. ........ 435/292.1 |
| 2007/0166816 | A1 | * | 7/2007 | Campbell et al. .......... 435/288.4 |
| 2007/0269814 | A1 | * | 11/2007 | Wilkes et al. ..................... 435/6 |
| 2008/0166753 | A1 | * | 7/2008 | Storey et al. .................... 435/32 |

* cited by examiner

*Primary Examiner* — Nathan Bowers
(74) *Attorney, Agent, or Firm* — Advent, LLP

(57) ABSTRACT

A system is provided that includes a tray having a number of compartments for holding liquid samples and partitioning the liquid samples from one another. The liquid samples are prepared by adding an indicator configured to produce a characteristic change in light from the liquid samples when a target microbe metabolizes the indicator while the liquid samples are incubated. The system also includes a light sensor for sensing light from the liquid samples held in the tray while the plurality of liquid samples is incubated. The system further includes a processor coupled with the light sensor and configured to analyze the light from the liquid samples while the liquid samples are incubated to detect the characteristic change in light from one or more of the liquid samples if the target microbe is present in the liquid samples.

8 Claims, 5 Drawing Sheets

FAST DETECTION OF THE PRESENCE OF A TARGET MICROBE IN A LIQUID SAMPLE

CROSS-REFERENCE TO RELATED APPLICATIONS

The present application claims the benefit under 35 U.S.C. §119(e) of U.S. Provisional Application Ser. No. 61/587,252, filed Jan. 17, 2012, and titled "FAST DETECTION OF THE PRESENCE OF A TARGET MICROBE IN A LIQUID SAMPLE," which is herein incorporated by reference in its entirety.

BACKGROUND

*Escherichia coli*, (commonly abbreviated *E. coli*) is a Gram-negative, rod-shaped bacterium that is commonly found in the lower intestine of warm-blooded organisms. Most *E. coli* strains are harmless, but some serotypes can cause food poisoning in humans, and are responsible for product recalls. For *E. coli* and related bacteria, fecal-oral transmission is the major route through which pathogenic strains of the bacterium cause disease. Cells are able to survive outside the body for a limited amount of time, which makes them ideal indicator organisms to test environmental samples for fecal contamination.

SUMMARY

A system for fast detection of the presence of a target microbe in a liquid sample is disclosed. In one or more implementations, the system includes a tray having a number of compartments for holding liquid samples and partitioning the liquid samples from one another. The liquid samples are prepared by adding an indicator configured to produce a characteristic change in light from the liquid samples when a target microbe metabolizes the indicator while the liquid samples are incubated. The system also includes a light sensor for sensing light from the liquid samples held in the tray while the plurality of liquid samples is incubated. The system further includes a processor coupled with the light sensor and configured to analyze the light from the liquid samples while the liquid samples are incubated to detect the characteristic change in light from one or more of the liquid samples if the target microbe is present in the liquid samples.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures.

DETAILED DESCRIPTION

Overview

Strains of *E. coli* are a major cause of foodborne illness. Generally, in order to detect *E. coli* and other microbes, samples must be taken from a suspected source and incubated over a period of time (e.g., eighteen (18) hours) in order to determine whether the suspected source is contaminated. After the incubation period, a tester must then manually examine each sample and record the results of each test. In some instances, this involves counting the number of individual samples that test positive and then comparing this result to a pre-specified number (e.g., when a concentration of biological contaminants must be measured, rather than the presence or absence of one or more of the contaminants). The long waiting time and the potential for error involved in counting and logging numbers of samples can lead to critical delays in the identification of potential sources of contamination. This may result in further contamination of a population and/or a wider spread of potentially contaminated goods.

Accordingly, techniques are described for fast detection of the presence (and/or absence) of a target microbe, such as *E. coli*, in a liquid sample. The techniques employ an automated system that includes a tray having a number of compartments for holding liquid samples and partitioning the liquid samples from one another. The liquid samples are prepared by adding an indicator configured to produce a characteristic change in light from the liquid samples when a target microbe metabolizes the indicator while the liquid samples are incubated. The system also includes a light sensor for sensing light from the liquid samples held in the tray while the plurality of liquid samples is incubated. The system further includes a processor coupled with the light sensor and configured to analyze the light from the liquid samples while the liquid samples are incubated to detect the characteristic change in light from one or more of the liquid samples if the target microbe is present in the liquid samples.

Example Implementations

Figure 1:
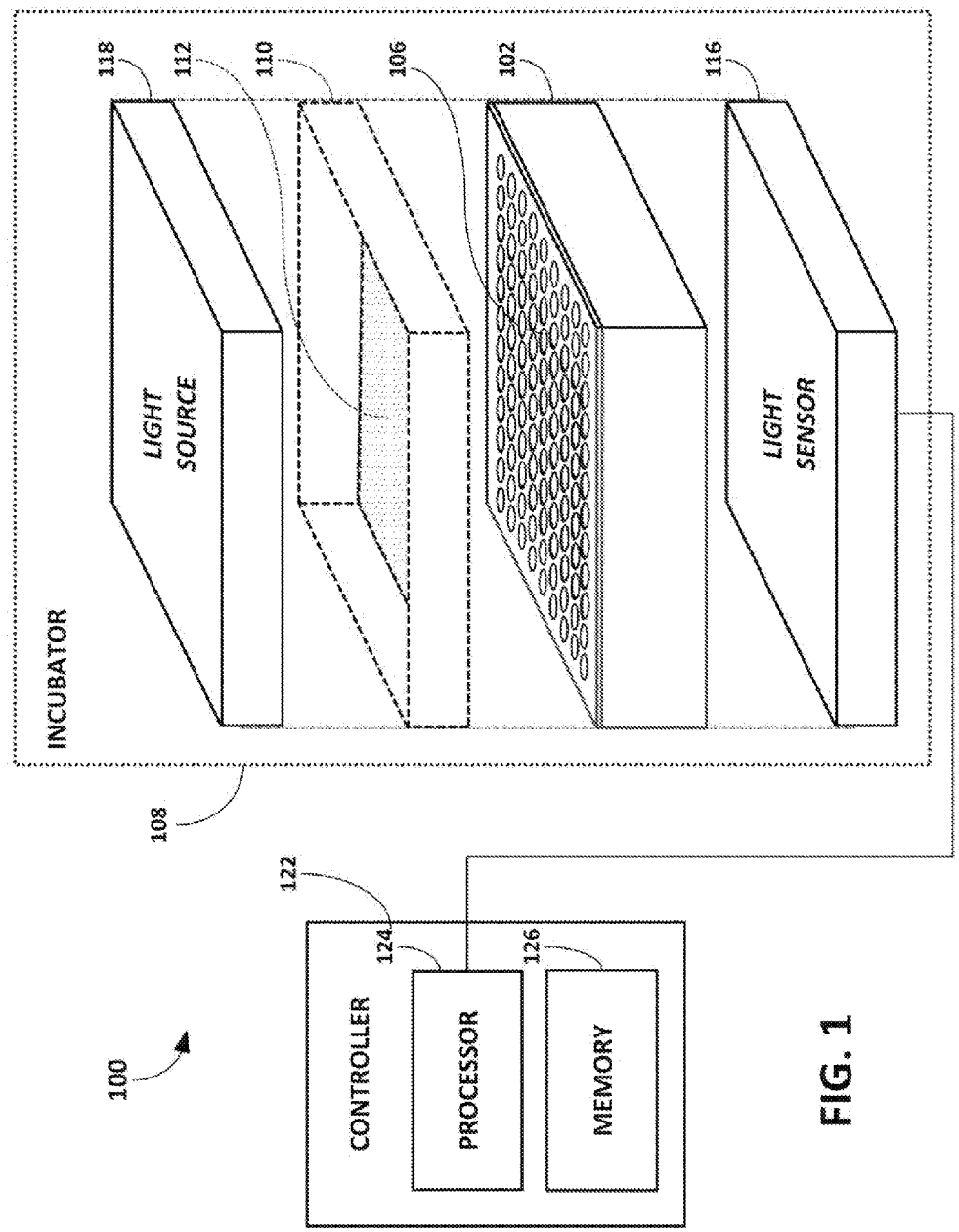
FIG. 1 is a schematic illustrating a system for automatically detecting the presence and/or absence of a target microbe in a liquid sample in accordance with example implementations of the present disclosure.
Figure 2:
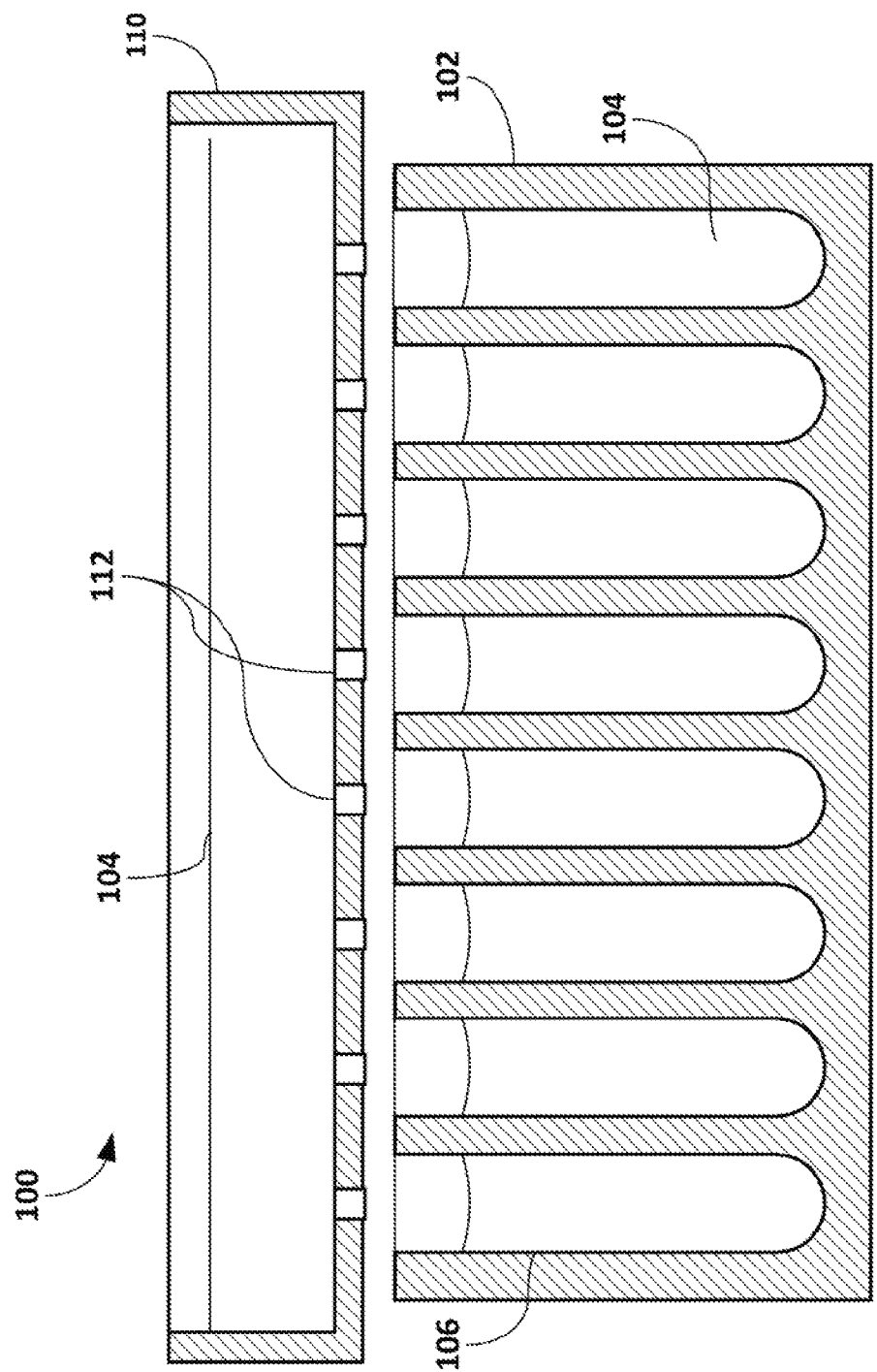
FIG. 2 is a cross-sectional side elevation view illustrating a tray for holding a number of individual liquid samples, along with a divider for portioning a bulk liquid sample into the individual liquid samples in accordance with example implementations of the present disclosure.

FIGS. 1 through 3 illustrate example systems 100 for detecting the presence and/or absence of a target microbe in a liquid sample in accordance with example implementations of the present disclosure.

It should be noted that for the purposes of the present disclosure, language such as "presence" and "absence," when used with respect to the detection (or lack thereof) of a target microbe, is not intended to be construed as limited to the detection of any quantity of the target microbe. Rather, the terms "presence" and "absence" are used to refer to both detection of one or more target microbes, as well as to quantification of microbial concentration of a target microbe within a sample (e.g., with respect to a pre-specified concentration). In some implementations, the presence of a target microbe within a sample may refer to the detection of any number of target microbes within the sample (e.g., when an example system 100 is used to detect a target microbe within a sample of potable water). Correspondingly, the absence of a target microbe within a sample may refer to the lack of detection of any number of target microbes within the sample. In other implementations, the presence of a target microbe within a sample may refer to the detection of a microbial concentration greater than a pre-specified concentration (e.g., when an example system 100 is used to detect a target microbe within a sample of waste water, incoming water for a water purification system, surface water, food testing, and so forth). Correspondingly, the absence of a target microbe within a sample may refer to the detection of a microbial concentration less than a pre-specified concentration. Further, a pre-specified concentration for establishing the presence and/or absence of a target microbe may be furnished by a user (e.g., via a user interface) and/or may be determined according to guidelines published by a regulatory agency (e.g., the Environmental Protection Agency (EPA), the Food and Drug Administration (FDA), and so forth).

An example system 100 includes a tray 102 for holding one or more liquid samples 104. The tray has a number of compartments 106 for holding and partitioning the liquid samples 104, keeping the liquid samples 104 separate from one another in the tray 102. For example, in one particular configuration, the tray 102 may comprise between about fifty and one hundred (50-100) compartments 106. However, this range is provided by way of example only and is not meant to be restrictive of the present disclosure. Thus, the tray 102 may comprise more than one hundred (100) or fewer than fifty (50) compartments 106. The compartments 106 can have various sizes/volumes. For example, in some instances, the compartments 106 may range in volume from about two one hundredths of a milliliter to about two milliliters (0.02 ml-2 ml). However, this range is provided by way of example only and is not meant to be restrictive of the present disclosure. Thus, the compartments 106 may have other various volumes. Further, all of the compartments 106 may have uniform (e.g., identical) volumes. However, it is contemplated that one set of compartments 106 (e.g., a group of twenty compartments) may each comprise one volume (e.g., two one hundredths of a milliliter (0.02 ml)), and another set of compartments 106 (e.g., another group of twenty compartments) may each comprise another volume (e.g., two milliliters (2 ml)). Further, in some implementations, the tray 102 can be at least substantially transparent, allowing light to pass from the liquid samples 104 through the material of the tray 102.

The liquid samples 104 are prepared by adding an indicator that produces a characteristic change in light (e.g., a change in light color in the visible spectrum, ultraviolet (UV) spectrum, infrared (IR) spectrum, and so forth) from the liquid samples 104 when a target microbe (e.g., *Escherichia coli* (*E. coli*)) is present in one or more of the liquid samples 104. In implementations, the characteristic change in light may be generated based upon the presence of discrete biological material within a sample that indicates the presence and/or absence of the target microbe, including, but not necessarily limited to: bacteria, fungi, living organisms, aggregates of proteins (e.g., enzymes, co-factors), and so forth. For example, a characteristic change in light may be produced when the target microbe metabolizes the indicator (e.g., while the liquid samples 104 are incubated). The liquid samples 104 can be incubated in, for instance, an incubator assembly 108.

In implementations, the indicator is a testing medium comprising a chemical and/or microbiological reactant. For instance, the indicator may comprise a reagent that fluoresces when exposed to ultraviolet (UV) light in the presence of *E. coli*. Further, the indicator can be a preferred or primary nutrient for a target microbe that cannot be substantially metabolized by other viable microbes that may be present in the sample. A growth accelerant can also be added to the liquid samples 104 to accelerate growth of the target microbe. The growth accelerant can be configured to boost the growth of the target microbes (and possibly other viable microbes) through a lag growth phase and toward a log growth phase. In implementations, other selective chemicals can also be provided, including antimetabolites, antibiotics, and so forth.

The system 100 may include a divider 110 for receiving a bulk liquid sample and portioning the sample into individual liquid samples 104. The bulk liquid sample can be prepared using one or more indicators, growth accelerants, and so forth (e.g., as previously described). In such implementations, the compartments 106 of the tray 102 can be configured to receive the liquid samples 104 from the divider 110. For instance, the divider 110 may comprise a second tray having side walls and a substantially porous, flat horizontal surface there between, where the surface is configured such that liquid introduced to the tray will evenly disperse across the flat surface and permeate through the pores to the compartments 106 of the tray 102. In some implementations, the tray 102 can be provided within a sealed package. This may reduce the possibility of exposing a tester to the liquid samples 104. For example, a liquid sample 104 can be poured into the divider 110 and dispersed into the compartments 106 of the tray 102. The tray 102 may then be placed within the package, and the package sealed. It is contemplated that the package may be fabricated of a material that is at least substantially transparent for allowing light to pass from the liquid samples 104 through the packaging material.

In implementations, the divider 110 can include an array of pores and/or channels 112, where, for example, one or more channels 112 correspond to each compartment of the tray 102. When a bulk liquid sample is poured into the tray, the liquid sample is portioned into the liquid samples 104 and flows through the channels 112 into the compartments 106 of the tray 102. It should be noted that the pores/channels 112 may be sized and/or shaped differently to accommodate differently sized compartments 106 of the tray 102. For example, smaller pores/channels 112 can be used to provide less liquid sample 104 material to smaller compartments 106, while comparatively larger pores/channels 112 can be used to provide more liquid sample 104 material to larger compartments 106. Further, in some implementations, channels 112 may be formed using one or more structures extending from the divider body. For example, channels 112 may be formed in tubes (e.g., pipettes) extending from the body of the divider 110. In some instances, pipettes may be configured to extend from the divider 110 some distance into one or more of the compartments 106 (e.g., extending just past the opening of a compartment, extending into a compartment 106 proximate to the bottom of the compartment, and so forth). In implementations, the divider 110 may comprise an autosampler assembly used to deliver one or more aliquots of a liquid sample 104 to each compartment 106 of the tray 102.

Figure 3A:
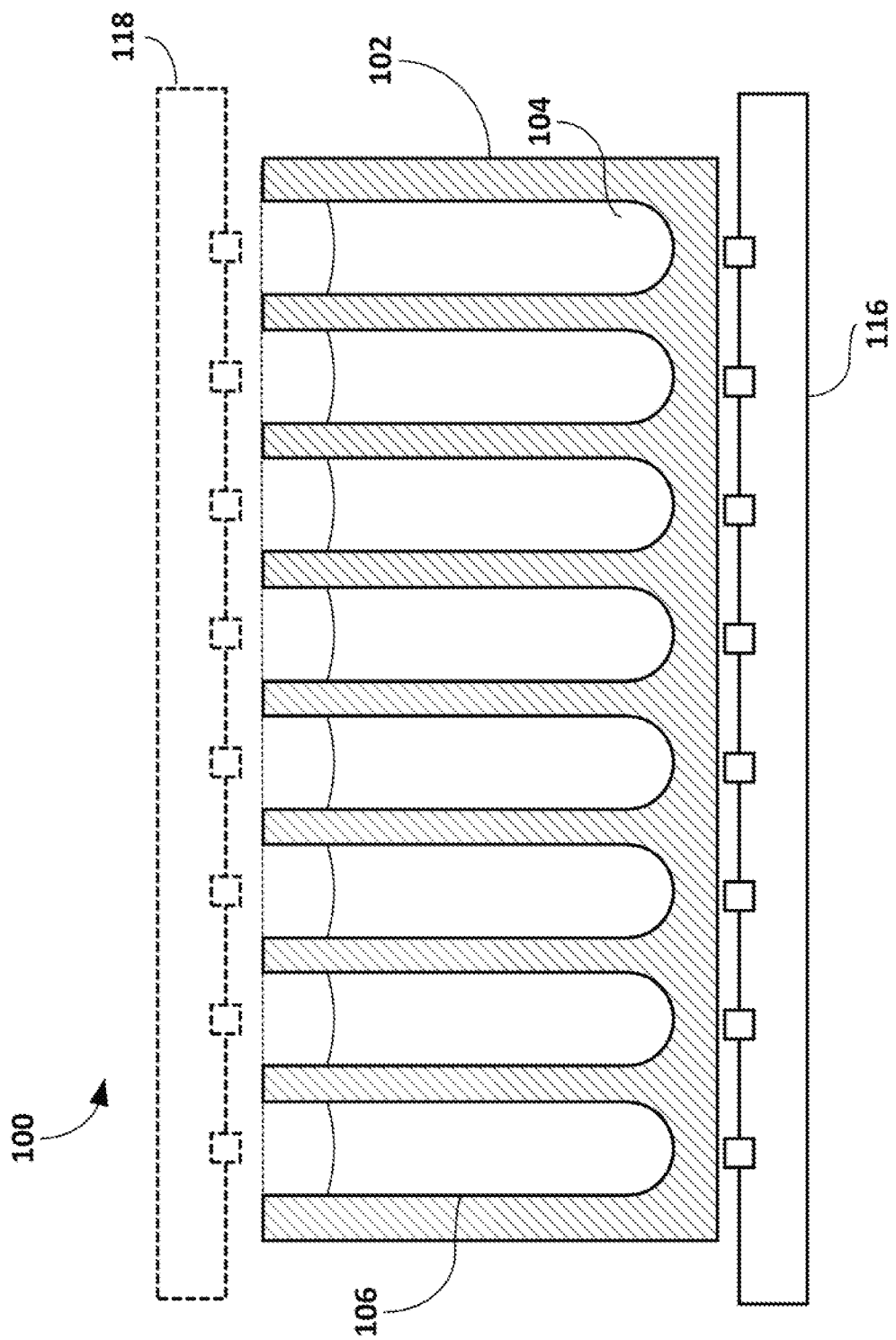
FIG. 3A is a schematic illustrating a tray for holding a number of individual liquid samples, along with a light source and a light sensor in accordance with example implementations of the present disclosure.

The system 100 also includes a light sensor 116 for sensing one or more characteristics of light from the liquid samples 104 held in the tray 102. In implementations, the light sensor 116 may be used to automatically sense light from the liquid samples 104 while the liquid samples 104 are incubated to provide real-time monitoring of the liquid samples 104 (e.g., during incubation of the liquid samples). The light sensor 116 may be configured as a photosensor/photodetector. For example, as shown in FIG. 3A, the light sensor 116 may comprise one or more photosensor diodes, phototransistors, and so forth. In implementations, the light sensor 116 is capable of detecting light and providing a signal in response thereto. Thus, the light sensor 116 may provide a signal by converting light into current and/or voltage based upon the intensity of the detected light. For example, when a light sensor 116 configured as a photodetector is exposed to light, multiple free electrons may be generated, creating a signal comprised of electrical current. The signal may correspond to one or more characteristics of the detected light, such as intensity (e.g., irradiance, etc.) of light incident upon the photodetector.

Figure 3B:
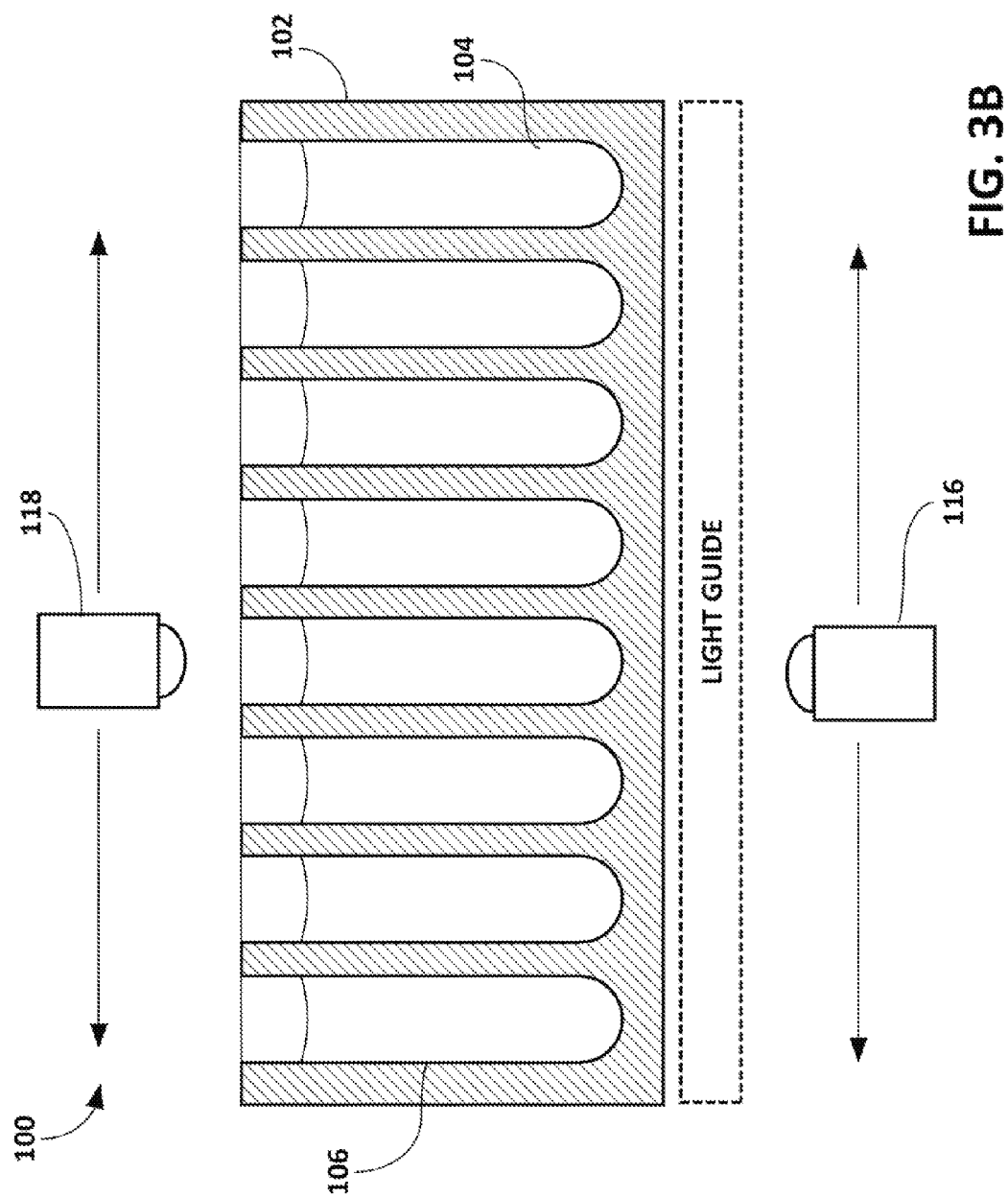
FIG. 3B is a schematic illustrating a tray for holding a number of individual liquid samples, along with a positionable light source and a positionable light sensor and light guide in accordance with example implementations of the present disclosure.

The light sensor 116 may comprise a Charge-Coupled Device (CCD), such as an image sensor sensitive to ultraviolet and/or visible light, an image capture device, such as a camera, and so forth. In implementations, the light sensor 116 may be configured to sense light from only a portion of the liquid samples 104 at a given instant in time. For instance, the light sensor 116 can be configured to sense light from the liquid samples 104 held in the compartments 106 one at a time. As shown in FIG. 3B, this can be implemented by a light sensor 116 configured to move from one compartment 106 or group of compartments 106 to another at a time, and/or by masking a group of compartments 106 from the light sensor 116. Further, separate portions of an image (e.g., regions of pixels from an image capture device) can be analyzed to determine light emitted from separate ones of the compartments 106. In implementations, the light sensor 116 can be used with a light guide configured to direct light from one or more of the compartments to the light sensor 116 (or to a specific detection region thereof). The light guide can be implemented as, for instance, an array of fiber optic cables, and so forth.

The system 100 may further include a light source 118 (e.g., one or more light emitting diodes for emitting visible light, UV light, and/or infrared light, as shown in FIG. 3A, a lamp for emitting visible light, UV light, and/or infrared light, as shown in FIG. 3B, combinations thereof, and so forth) for illuminating the liquid samples 104 held in the compartments 106 of the tray 102. In implementations, the light source 118 may be configured to illuminate only a portion of the liquid samples 104 at a given instant in time. For instance, the light source 118 can be configured to illuminate the liquid samples 104 held in the compartments 106 one at a time. This can be implemented by a light source 106 that includes a plurality of LEDs which may be switched on and off, as shown in FIG. 3A, or by a light source 118 configured to move from one compartment 106 or group of compartments 106 to another at a time, as shown in FIG. 3B, and/or by masking a group of compartments 106 from the light source 118. The light source 118 can be used to provide sufficient light for the light sensor 116 to measure a characteristic change in light from the liquid samples 104. For instance, a UV light source 118 may be used to cause a reagent to fluoresce when exposed to ultraviolet (UV) light in the presence of a target microbe such as *E. coli*.

The system 100 further includes a processor 124 coupled with the light sensor 116. The processor 124 is configured to analyze one or more characteristics of the light from the liquid samples 104 as sensed by the light sensor 116 to detect the characteristic change in light from the liquid samples 104 if the target microbe is present. For instance, the system 100 may comprise an electronic device/controller 122, which may include the processor 124, memory 126, and so forth. The processor 124 provides processing functionality for the electronic device 122 and may include any number of processors, micro-controllers, or other processing systems and resident or external memory for storing data and other information accessed or generated by the electronic device 122. The processor 124 may execute one or more software programs which implement the techniques and modules described herein. The processor 124 is not limited by the materials from which it is formed or the processing mechanisms employed therein and, as such, may be implemented via semiconductor(s) and/or transistors (e.g., electronic Integrated Circuits (ICs)), and so forth.

The memory 126 is an example of device-readable storage media that provides storage functionality to store various data associated with the operation of the electronic device 122, such as the software program and code segments mentioned above, or other data to instruct the processor 124 and other elements of the electronic device 122 to perform the techniques described herein. Although a single memory 126 is shown, a wide variety of types and combinations of memory may be employed. The memory 126 may be integral with the processor 124, stand-alone memory, or a combination of both. The memory 126 may include, for example, removable and non-removable memory elements such as Random Access Memory (RAM), Read Only Memory (ROM), Flash memory (e.g., a Secure Digital (SD) card, a mini-SD card, a micro-SD card), magnetic memory, optical memory, Universal Serial Bus (USB) memory devices, and so forth. In embodiments of the electronic device 122, the memory 126 may include removable Integrated Circuit Card (ICC) memory, such as memory provided by Subscriber Identity Module (SIM) cards, Universal Subscriber Identity Module (USIM) cards, Universal Integrated Circuit Cards (UICC), and so on.

In implementations, the processor 124 may be used to automatically analyze characteristics of the light from the liquid samples 104 while the liquid samples 104 are incubated to provide real-time analysis of the liquid samples 104 for detecting the presence and/or the absence of the target microbe. For example, the processor 124 can be configured to automatically identify the presence of the target microbe in the liquid samples 104 as soon as the characteristic change in light is detected for a pre-specified number of the liquid samples 104, which may correspond to, for instance, a concentration of the target microbe within the liquid samples 104. The pre-specified number of the liquid samples 104 can be stored in the memory 126. This may allow the presence and/or the absence of the target microbe to be determined more quickly (e.g., without having to wait for the entirety of the incubation period).

In implementations, the most probable number method can be used to determine a pre-specified number of liquid samples 104 in which a characteristic change in light is needed to identify the presence and/or absence of the target microbe. For example, a pre-specified number of liquid samples 104 can be determined using one or more techniques described in Recles et al., "Most Probable Number Techniques" published in "Compendium of Methods for the Microbiological Examination of Foods", 3rd ed. 1992, at pages 105-199, and/or in Greenberg et al., "Standard Methods For the Examination of Water and Wastewater" (8th ed. 1992).

Statistical techniques can be used to project whether a particular group of liquid samples 104 is likely to test positive (or negative) for the presence and/or the absence of a particular target microbe within an incubation period for which the pre-specified number of liquid samples 104 has been determined (e.g., using techniques referred to above). For example, if a characteristic change in light is identified for a certain number of liquid samples 104 less than the pre-specified number before the end of an incubation period, but within an intermediate time interval, the liquid samples 104 may be identified as containing a concentration of target microbes necessary to establish their presence within the liquid samples 104. Further, the likely presence of the sample microbe may be returned as an intermediate result, alerting a tester that the presence of the target microbe is likely indicated for the liquid samples 104. Correspondingly, if a characteristic change in light is not identified for a certain number of liquid samples 104 less than the pre-specified number before the end of an incubation period, but within an intermediate time interval, the liquid samples 104 may be identified as containing a concentration of target microbes insufficient to establish their presence within the liquid samples 104. Further, the likely absence of the sample microbe may be returned as an intermediate result, alerting a tester that the absence of the target microbe is likely indicated for the liquid samples 104.

Example Process

Figure 4:
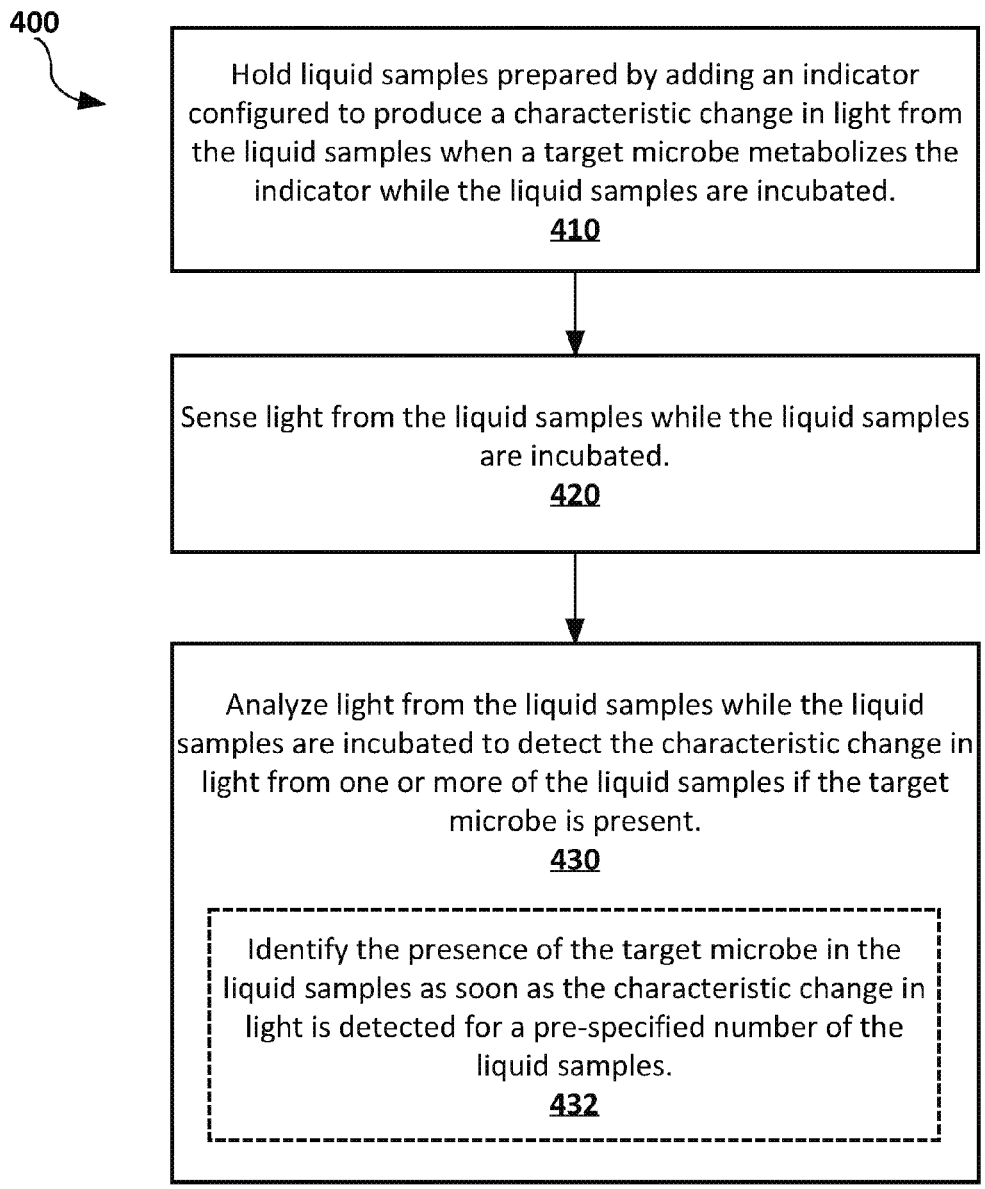
FIG. 4 is a flow diagram illustrating a method for automatically detecting the presence and/or absence of a target microbe in a liquid sample in accordance with example implementations of the present disclosure.

Referring now to FIG. 4, example techniques for detecting the presence and/or absence of a target microbe in a liquid sample are described.

FIG. 4 depicts a process 400, in an example implementation, for detecting the presence and/or absence of a target microbe in a liquid sample using, for example, the system 100 illustrated in FIGS. 1 through 3 and described above. In the process 400 illustrated, one or more liquid samples are held, where the liquid samples have been prepared by adding an indicator configured to produce a characteristic change in light from the plurality of liquid samples when a target microbe metabolizes the indicator while the plurality of liquid samples is incubated (Block 410). For example, with reference to FIGS. 1 through 3, liquid samples 104 can be prepared by adding an indicator that produces a characteristic change in light (e.g., a change in light color in the visible spectrum, ultraviolet (UV) spectrum, infrared (IR) spectrum, and so forth) from the liquid samples 104 when a target microbe (e.g., *Escherichia coli* (*E. coli*)) is present in one or more of the liquid samples 104. The liquid samples 104 can be held in tray 102 having compartments 106 for partitioning the liquid samples 104, keeping the liquid samples 104 separate from one another in the tray 102. The tray 102 can be held in incubator assembly 108 while the liquid samples 104 are incubated.

Light can be automatically sensed from the liquid samples while the liquid samples are incubated (Block 420). For instance, with continuing reference to FIGS. 1 through 3, light sensor 116 can be used to sense one or more characteristics of light from the liquid samples 104 held in the tray 102. The light sensor 116 can be used to automatically sense light from the liquid samples 104 while the liquid samples 104 are incubated to provide real-time monitoring of the liquid samples 104. The light sensor 116 may be configured as a photosensor/photodetector, an image capture device, and so forth.

One or more characteristics of the light from the liquid samples can be automatically analyzed while the liquid samples are incubated to detect the characteristic change in light from one or more of the liquid samples if the target microbe is present (Block 430). For example, with continuing reference to FIGS. 1 through 3, system 100 may further include processor 124 coupled with the light sensor 116. The processor 124 can be used to automatically analyze characteristics of the light from the liquid samples 104 while the liquid samples 104 are incubated to provide real-time analysis of the liquid samples 104 for detecting the presence and/or the absence of the target microbe. Thus, in some implementations, the presence of the target microbe in the liquid samples can be determined as soon as the characteristic change in light is detected for a pre-specified number of the liquid samples (Block 432). For example, the processor 124 can be configured to automatically identify the presence of the target microbe in the liquid samples 104 as soon as the characteristic change in light is detected for a pre-specified number of the liquid samples 104, which may correspond to, for instance, a concentration of the target microbe within the liquid samples 104.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A system for detecting the presence of a target microbe comprising:
   a tray configured to be received in an incubator for holding liquid samples during incubation, each of the liquid samples including an indicator configured to produce a characteristic change in light from the liquid sample when a target microbe metabolizes the indicator during incubation of the liquid sample, the tray including a plurality of compartments configured to partition the liquid samples one from another;
   a light sensor for individually sensing light from each of the liquid samples held separately in the plurality of compartments of the tray during incubation of the liquid samples, the light sensor configured to detect a characteristic of the light sensed from each of the separately held liquid samples; and
   a controller coupled with the light sensor, the controller configured to analyze the detected characteristic of the light sensed from each of the separately held liquid samples to detect occurrences of the characteristic change in light from respective ones of the separately held liquid samples as the separately held liquid samples are incubated, the controller furnishing an indication that presence of the target microbe is detected while the separately held liquid samples are being incubated when a detected number of occurrences of the characteristic change in light, corresponding to a number of separately held liquid samples, exceeds a threshold number of occurrences of the characteristic change in light from respective ones of a total number of separately held liquid samples, the threshold number of occurrences of the characteristic change in light from respective ones of the total number of separately held liquid samples corresponding to a concentration of the target microbe within the liquid samples that indicates presence of the target microbe,
   wherein the concentration of the target microbe within the separately held liquid samples is indicated by the occurrence of the characteristic change in light from a predetermined number of the separately held liquid samples following a predetermined incubation period, and wherein the threshold number of occurrences of the characteristic change in light from respective ones of the total number of separately held liquid samples is less than the predetermined number for an intermediate time period less than the predetermined incubation period, and
   wherein the controller furnishes an indication of the absence of the target microbe if the detected number of occurrences of the characteristic change in light from respective ones of the total number of separately held liquid samples does not exceed the threshold number of occurrences of the characteristic change in light from respective ones of the total number of separately held liquid samples within the intermediate time period.

2. The system as recited in claim 1, wherein the liquid samples further include a growth accelerant for accelerating growth of the target microbe.

3. The system as recited in claim 1, wherein the target microbe comprises *Escherichia coli* (*E. coli*).

4. The system as recited in claim 1, further comprising a divider for receiving a single liquid sample and equally portioning the single liquid sample into the liquid samples, the plurality of compartments of the tray configured for receiving the liquid samples from the divider.

5. The system as recited in claim 1, further comprising a light source configured to be received in the incubator for illuminating the liquid samples held in the plurality of compartments during incubation of the liquid samples.

6. The system as recited in claim 5, wherein the light source is configured to individually illuminate one of the liquid samples held in the plurality of compartments at a time.

7. A system for detecting the presence of a target microbe comprising:
- a tray configured to be received in an incubator for holding liquid samples during incubation, each of the liquid samples being separately held in the tray and including an indicator configured to produce a characteristic change in light from a respective one of the separately held liquid samples when a target microbe metabolizes the indicator;
- a light sensor for sensing light from the separately held liquid samples tray during incubation of the liquid samples, the light sensor configured to detect a characteristic of the light sensed; and
- a controller coupled with the light sensor, the controller configured to analyze the detected characteristic of the light sensed from the separately held liquid samples to detect occurrences of the characteristic change in light from respective ones of the separately held liquid samples, the controller furnishing an indication that presence of the target microbe is detected while the separately held liquid samples are being incubated when a detected number of occurrences of the characteristic change, corresponding to a number of separately held liquid samples, exceeds a threshold number of occurrences of the characteristic change in light from respective ones of a total number of separately held liquid samples, the threshold number of occurrences of the characteristic change in light from respective ones of the total number of separately held liquid samples corresponding to a concentration of the target microbe within the liquid samples that indicates presence of the target microbe,
- wherein the concentration of the target microbe within the separately held liquid samples is indicated by the occurrence of the characteristic change in light from a predetermined number of the separately held liquid samples following a predetermined incubation period, and wherein the threshold number of occurrences of the characteristic change in light from respective ones of the total number of separately held liquid samples is less than the predetermined number for an intermediate time period less than the predetermined incubation period, and
- wherein the controller furnishes an indication of the absence of the target microbe if the detected number of occurrences of the characteristic change in light from respective ones of the total number of separately held liquid samples does not exceed the threshold number of occurrences of the characteristic change in light from respective ones of the total number of separately held liquid samples within the intermediate time period.

8. The system as recited in claim 7, wherein the liquid samples further include a growth accelerant for accelerating growth of the target microbe.

* * * * *